United States Patent [19]

Gan et al.

[11] Patent Number: 5,843,396
[45] Date of Patent: Dec. 1, 1998

[54] METHOD FOR STABILIZING RADIOLABELED ORGANIC COMPOUNDS BY ADDING A SEPARATE STABILIZING COMPOUND

[75] Inventors: Nadine Michele Loretta Gan, Newtown Centre; Gary Thomas Overmeyer, Tewksbury; Douglas Roger Dennistoun Shaw, Cambridge, all of Mass.

[73] Assignee: Nen Life Science Products, Inc., Boston, Mass.

[21] Appl. No.: 763,428

[22] Filed: Dec. 11, 1996

Related U.S. Application Data

[62] Division of Ser. No. 496,147, Jun. 28, 1995, abandoned.
[51] Int. Cl.⁶ ............................. A61K 51/00; C07F 5/00; C07K 16/00
[52] U.S. Cl. ...................... 424/1.41; 424/1.45; 424/1.49; 424/1.65; 424/1.69; 424/1.73; 424/1.53; 530/391.3; 534/10
[58] Field of Search .................... 424/1.11, 1.65, 424/1.41, 1.53, 1.49, 1.81, 1.37, 1.45, 1.69, 1.73; 536/26.6; 534/10, 14; 530/391.3

[56] References Cited

U.S. PATENT DOCUMENTS

| | | | |
|---|---|---|---|
| 4,358,434 | 11/1982 | Tzodikov et al. | 424/1.1 |
| 4,390,517 | 6/1983 | O'Brien et al. | 424/1.1 |
| 4,411,881 | 10/1983 | Tzodikov | 424/1.1 |
| 4,451,451 | 5/1984 | Rimmer | 424/1.1 |
| 4,793,987 | 12/1988 | Henderson et al. | 424/1.1 |
| 5,118,499 | 6/1992 | Theodoropulos | 424/78.23 |
| 5,284,644 | 2/1994 | Kruper, Jr. et al. | 424/1.53 |
| 5,393,512 | 2/1995 | Vanderheyden et al. | 424/1.53 |
| 5,395,608 | 3/1995 | Troutner et al. | 424/1.49 |
| 5,494,654 | 2/1996 | Price et al. | 424/1.65 |
| 5,514,363 | 5/1996 | Shochat et al. | 424/1.49 |

FOREIGN PATENT DOCUMENTS

| | | | |
|---|---|---|---|
| 93/22260 | 11/1993 | WIPO | C07B 59/00 |

OTHER PUBLICATIONS

Etlis, V. S. et al., Synthesis and Antiradiation Properties of Polymeric Dithiocarbamates, *Khimiko–Farmatsevticheskii Zhurnal*, 10, No. 4, pp. 452–453, Apr. 1976.

Barnes, J. H. et al., Synthesis and Radioprotective Effects of the Disodium Alkanebisdithiocarbamates of ω–aminoalkyldithiocarbamic Acids and Their N,N'–dimethyl Derivatives, *Eur. J. Med. Chem.–Chimica Therapeutica*, 10, No. 6, pp. 619–622, Nov.–Dec. 1975.

Sheppard, G., The Self–Decomposition of Radioactively Labelled Compounds, *Atomic Energy Review*, pp. 3–66, 1972 Without Month.

Liebster J. and Kopoldova J., The Radiation Chemistry of Amino Acids, *Radiation Biology*, pp. 157–226, 1964.

Nagai, K. et al., Apparatus For Base Sequence Determination in Nucleic Acids, *Chemical Abstracts*, 111:93463b, p. 388, 1989.

*Primary Examiner*—Gary E. Hollinden
*Assistant Examiner*—Michael G. Hartley
*Attorney, Agent, or Firm*—Gifford, Krass, Groh, Sprinkle, Patmore, Anderson & Citkowski, P.C.

[57] ABSTRACT

A stabilized composition comprising an organic compound labeled with a β-emitting radionuclide and a stabilizing effective amount of a non-radiolabeled stabilizing compound selected from the group consisting of (i) heteroaryls having at least one nitrogen atom, said heteroaryl being substituted with at least one sulfur-containing moiety selected from the group consisting of thiol and thiocarbonyl provided that the nitrogen atoms are not adjacent to one another; (ii) aryls being substituted with at least one nitrogen-containing moiety selected from the group consisting of amino and isothiocyanate and with at least one sulfur-containing moiety selected from the group consisting of sulfonamide, sulfonate, and thiol; and (iii) alkylamines having at least one to four carbon atoms, said alkylamine being substituted with at least one sulfur-containing moiety selected from the group consisting of thioacid and thiocarbonyl provided that when the sulfur-containing moiety is a thioacid then the aminoalkyl contains only one nitrogen atom.

8 Claims, No Drawings

METHOD FOR STABILIZING RADIOLABELED ORGANIC COMPOUNDS BY ADDING A SEPARATE STABILIZING COMPOUND

This is a division of application Ser. No. 08/496,147, filed Jun. 28, 1995, now abandoned.

FIELD OF THE INVENTION

This invention relates to the stabilization of radiolabeled compounds and, more particularly, to a composition and method for stabilizing radiolabeled organic compounds.

BACKGROUND OF THE INVENTION

An increasing number of radiolabeled compounds are being used in research for medical diagnosis and various other areas. However, the radiolytic decomposition of such compounds has been a constant problem. Without the addition of some type of stabilizer, a solution of such a compound may become unusable due to decomposition within a matter of weeks or less. This radiolytic decomposition of such compounds has been studied extensively. For example, the radiation chemistry of amino acids is reviewed in an article by J. Liebster and J. Kopeldova, *Radiation Biol.*, 1, 157 (1964) and the self-decomposition of radiolabeled compounds is discussed in *Atomic Energy Review*, 10, 3–66 (1972), both of which are hereby incorporated herein by reference.

Although certain specific compounds have been suggested for stabilization, problems still exist. The latter article reviews the underlying causes and mechanisms of self-decomposition, "which are very complex and in some cases not well understood." (At pg. 3). After discussing the principal mechanisms by which decomposition occurs, the article notes generally at page 36 that buffers such as ammonium bicarbonate help to stabilize radiolabeled compounds, but care must be taken to insure that the buffer chosen does not interfere with the later use of the labeled compound. For example, phosphate buffers would interfere with phosphorylation reactions. Other compounds which have been suggested as stabilizers at various times are listed at page 35 and include benzyl alcohol, glycerol, cysteamine, and sodium formate. However, each of these are said to suffer due to their difficulty of removal. Another compound mentioned is ethanol which is said to work with many compounds. However, ethanol sometimes actually sensitizes certain nucleosides to radiation decomposition and thus it has been found not to be a universal panacea. Furthermore, if it will interfere with the reaction in which the radiolabeled compound is to be used, the ethanol must be removed by evaporation which may also contribute to decomposition.

Various compounds are suggested in *Atomic Energy Review*, above, for stabilization of radiolabeled compounds prone to oxidation including antioxidants such as butylated-hydroxytoluene, butylated-hydroxyanisole and mercaptoethanol. While not mentioned for use with radiolabeled compounds, the inhibition of autoxidation generally by certain amines has also been described in the prior art. Recent reviews on the inhibition of autoxidation are "Autoxidation" by R. Stroh, pg. 1049 in *Methoden der Organischen Chemie* (Houben-Weyl), ed. E. Muller and O. Bayer, Vol. IV/Ib Oxidation II., Georgthieme Verlag, 1975, and *Encyclopedia of Chemical Technology*, Kirk Othmer, Interscience Publishers, New York. The utility of secondary dialkyl amines bearing full alpha-substitution (i.e., containing no hydrogens on the carbon atoms adjacent to the nitrogen) and secondary diarylamines (also without alpha-hydrogens) as antioxidants is known.

U.S. Pat. No. 4,793,987 describes stabilized radiolabeled compounds using pyridine carboxylic acids as stabilizers.

U.S. Pat. No. 4,451,451 describes the use of 4-aminobenzoic acid as an antioxidant in compositions containing Technetium-99m.

U.S. Pat. No. 4,411,881 describes the use of thiocarbonylated amines as stabilizers.

PCT International Application having International Publication No. WO 93/22260 published Nov. 11, 1993 describes radiolabeled compound formulations which are stabilized using tryptophan, para-aminobenzoate, indoleacetate, luminol and the group of azoles which are compounds having a 5-membered ring with at least two ring nitrogen atoms directly bonded to one another.

U.S. Pat. No. 3,876,550 describes lubricant compositions to improve the anti-oxidant and rust inhibiting properties of such lubricant compositions. The additive combination includes alkylene dithiocarbamate, but does not contain any suggestion for the use of such compounds as stabilizers for radiolabeled compounds.

V. S. Etlis et al., "Synthesis and Anti-Radiation Properties of Polymeric Dithiocarbamates", *Khimiko-Farmatsevicheskii Zhurnal*, Vol. 10, No. 4, pp. 33–35, April (1976) describes the synthesis and preparation of water soluble polymeric sodium and ammonium dithiocarbamates, indicates that they are useful as radiation protectors, and reports testing of such compounds in mice for protection against irradiation with $Co^{60}$ (1000 R, intensity 26–30 R/sec.). However, these compounds are not indicated as having any activity as stabilizers of radiolabeled compounds.

J. Barnes et al., *Eur. J. Med. Chem. - Chimica Therapeutica*, November December (1975)-10, No. 6, pgs. 619–622, describes sodium salts of alkenebisdithiocarbamates and aminoalkyldithiocarbamic acids for use as radiation protection agents. The compounds were tested in mice for use as radio-protectors. Particular attention is called to compound No. 11 in Table 1 on page 620, the preparation of which is described on page 621 in the paragraphs immediately below Table 2. It is believed that the structure of compound 11 is incorrectly identified. There is no disclosure or suggestion in Barnes et al., for employing any of the compounds therein for the stabilization of radiolabeled compounds and solutions.

U.S. Pat. No. 4,358,434 and U.S. Pat. No. 4,390,517, both of which are incorporated herein by reference, disclose the stabilization of radiolabeled compounds by adding to solutions of such compounds a compound having a substantially insoluble backbone, preferably a resin, such as an ion exchange resin, to which has been bound a quaternary ammonium group; or a water soluble primary, secondary or tertiary aliphatic amine which does not interfere with the use contemplated for the particular radiolabeled compound being stabilized.

SUMMARY OF THE INVENTION

The present invention concerns a composition comprising an organic compound labeled with a β-emitting radionuclide and a stabilizing effective amount of a non-radiolabeled stabilizing compound selected from the group consisting of (i) heteroaryls having at least one nitrogen atom, said heteroaryl being substituted with at least one sulfur-containing moiety selected from the group consisting of thiol and thiocarbonyl provided that the nitrogen atoms are not adjacent to one another; (ii) aryls being substituted with at least one nitrogen-containing moiety selected from the group consisting of amino and isothiocyanate and with at least one sulfur-containing moiety selected from the group consisting of sulfonamide, sulfonate, and thiol; and (iii) alkylamines having at least one to four carbon atoms, said alkylamine being substituted with at least one sulfur-containing moiety selected from the group consisting of thioacid and thiocarbonyl provided that when the sulfur-containing moiety is a thioacid then the aminoalkyl contains only one nitrogen atom.

In another embodiment the invention concerns a composition for stabilizing an organic compound labelled with a β-emitting radionuclide against radiolytic degradation during storage and shipment which comprises an organic compound labelled with a β-emitting radionuclide and a stabilizing effective amount of rhodanine-3-acetic acid.

In still another embodiment the invention concerns a method for stabilizing a solution of an organic compound labelled with a β-emitting radionuclide against radiolytic degradation during storage and shipment which comprises adding to said solution a stabilizing effective amount of a non-radiolabeled stabilizing compound selected from the group consisting of (i) heteroaryls having at least one nitrogen atom, said heteroaryl being substituted with at least one sulfur-containing moiety selected from the group consisting of thiol and thiocarbonyl provided that the nitrogen atoms are not adjacent to one another; (ii) aryls being substituted with at least one nitrogen-containing moiety selected from the group consisting of amino and isothiocyanate and with at least one sulfur-containing moiety selected from the group consisting of sulfonamide, sulfonate, and thiol; and (iii) alkylamines having at least one to four carbon atoms, said alkylamine being substituted with at least one sulfur-containing moiety selected from the group consisting of thioacid and thiocarbonyl provided that when the sulfur-containing moiety is a thioacid then the aminoalkyl contains only one nitrogen atom.

This invention also concerns a method of stabilizing a solution of an organic compound labelled with a β-emitting radionuclide against radiolytic degradation during storage and shipment which comprises adding to said solution a stabilizing effective amount of rhodanine-3-acetic acid.

DETAILED DESCRIPTION OF THE INVENTION

Radiolabeled nucleotides and other organic compounds are conventionally shipped and stored at −20° C. or below, requiring the use of dry ice.

The present invention provides a composition and method for stabilizing radiolabeled organic compounds to permit the shipment and storage of such compounds either at 4° C. (on ice) or more preferably at ambient temperature. The composition comprises an organic compound labelled with a β-emitting radionuclide and a stabilizing effective amount of a non-radiolabeled stabilizing compound selected from the group consisting of (i) heteroaryls having at least one nitrogen atom, said heteroaryl being substituted with at least one sulfur-containing moiety selected from the group consisting of thiol and thiocarbonyl provided that the nitrogen atoms are not adjacent to one another; (ii) aryls being substituted with at least one nitrogen-containing moiety selected from the group consisting of amino and isothiocyanate and with at least one sulfur-containing moiety selected from the group consisting of sulfonamide, sulfonate, and thiol; and (iii) alkylamines having at least one to four carbon atoms, said alkylamine-being substituted with at least one sulfur-containing moiety selected from the group consisting of thioacid and thiocarbonyl provided that when the sulfur-containing moiety is a thioacid then the aminoalkyl contains only one nitrogen atom.

Examples of heteroaryl stabilizing compounds (i) which can be used to practice the invention include, but are not limited to, trithiocyanuric acid, 2-mercaptonicotinic acid, 2-mercaptoimidazole, 2-mercapto-1-methylimidazole, 4-amino-2-mercaptopyrimidine, 2-mercaptopyrimidine, 4-mercaptopyridine, and 2-mercaptopyridine.

Examples of aryl stabilizing compounds (ii) which can be used to practice the invention include, but are not limited to, aminobenzenesulfonamide, 3-aminothiophenol, and 4-sulfonylphenyl isothiocyanate.

Examples of alkylamine stabilizing compounds (iii) which can be used to practice the invention include, but are not limited to, dimethyldithiocarbamic acid, thiosemicarbazide, 4-morpholinoethylthiosemicarbazide, 4-methylthiosemicarbazide, 4,4-dimethylthiosemicarbazide, acetone thiosemicarbazone, and 2,5,-dithiobiurea.

A further example of a stabilizing compound which can be used to practice the invention is rhodanine-3-acetic acid.

A "stabilizing effective amount" as used herein means any amount of the stabilizer compounds of this invention which is beneficial in preventing the decomposition of radiolabeled compounds. It is preferred, however, that the stabilizing compound be present at concentrations in the range of about 0.1 millimolar (mM) to about 200 millimolar depending on the specific activity of the radiolabeled compound, the concentration of the radiolabeled compound in the solution, and the particular radioisotope being employed as the label. Preferably, the concentration is in the range of about 1 millimolar to 100 millimolar.

The method of the present invention can be used with any of the solvents typically used to store radiolabeled compounds such as water, ethanol, mixtures of water and ethanol in any ratio, dilute mineral and organic acids, buffers and other such solvents employed in the prior art.

The present invention can be used to prevent the decomposition of radiolabeled compounds which have been labeled with any of the radionuclides used for such purposes, including tritium, carbon-14, phosphorus-32, phosphorus-33, sulfur-35, and the various radioisotopes of iodine, including iodine-125. In addition, the present invention helps to stabilize radiolabeled compounds for shipment and storage either at 4° C. (on ice) or more preferably at ambient temperature.

The radiolabeled compound may be any of those subject to radiolytic decomposition, such as radiolabeled amino acids, catecholamines, nucleotides, polynucleotides, oligonucleotides, nucleosides, nucleoside phosphorothioates, proteins, peptides, polypeptides, carbohydrates, drugs, lipids, fatty acids, steroids, and the like.

Examples of such radiolabeled compounds include but are not limited to the following: Abscisic acid, (±)cis, trans-[2-$^{14}$C]-; Acetaminophen; Acetyl-2-aminofluorene, N-[9-$^{14}$C]-; Acetyl Concanavalin A; Acetyl-5-methoxytryptamine, N-[2-aminoethyl-2-$^{3}$H]-; Acetylsalicylic acid,[carboxyl-$^{14}$C]-; α-Acid glycoprotein, [$^{125}$I]-; ACTH; Adrenocorticotropic hormone, [$^{125}$I]-(human); ADTN; Albumin (bovine serum), [$^{125}$I]-; Allynormetazocine; Alprenolol; Amethopterin; Aminoclonidine,p-[3,5-$^{3}$H]-; Amino-6,7-dihydroxy-1,2,3,4-tetrahydronaphthalene,2-:-[5,8-$^{3}$]-; Aminopyrine,

[dimethylamine-$^{14}$C]-; Amino-12,4-triazole, 3-[5-$^{14}$C]-; Amphetamine sulfate, D-[$^{3}$H(G)]-; Angiotensin III (4-L-isoleucine),[tyrosyl-3,5-$^{3}$H(N)]-; Angiotensin II (5-L-isoleucine), [tyrosyl-3,5-$^{3}$H(N))]-; Angiotensin II (5-L-isoleucine), [tyrosyl-$^{125}$I]-(monoiodinated); Angiotensin I (5-L-isoleucine), [tyrosyl-$^{125}$I]-(monoiodinated); Antipyrine, [N-methyl-$^{14}$C]-; Apomorphine, L-(−)-[8,9-$^{3}$H]-; Ascorbic acid, L-[1-$^{14}$C]-; Benzene hexachloride, γ-[$^{14}$C(U)]-; Benzidine, [$^{14}$C(U)]-; Benzo[a]pyrene, [1,3,6-$^{3}$H]-; Bovine serum albumin; Bradykinin, [2,3-prolyl-3,4-$^{3}$H(N)]-; Bradykinin (8-tyrosine)-triacetate, [8-tyrosyl-$^{125}$I]-; α-Bungarotoxin, [$^{125}$I]-; Caffeine, [1-methyl-$^{14}$C]-; Capsaicin; Carazolol, DL-[3,6-$^{3}$H(N)]-; Chloramphenicol, [dichloracetyl-1,2$^{14}$C]-; Chloroquine, dip[phosphate salt], [ring-3-$^{14}$C]-; Chlorpromazine hydrochloride, [benzene ring-$^{3}$H]-; Clonidine hydrochloride, [4-$^{3}$H]-; Cocaine, leyo-[benzoyl-3,4-$^{3}$H(N)]-; Coenzyme A, [$^{3}$H(G)]-; Colchicine, [ring C, methoxy-$^{14}$C]-; Colchicine, [ring C,methoxy-$^{3}$H]-; Concanavalin A, [$^{3}$H(G)]-; Concanavalin A [$^{125}$I]-; Concanavalin A, N-[acetyl-$^{3}$H]acetylated-; Cyclohexenyl-3,5-dimethylbarbituric acid, 5-[2-$^{14}$C]-; Cyclohexyladenosine, N$^{8}$-[adenine-2,8-$^{3}$H]-; Cyclophosphamide, [ring-4-$^{14}$C]-; Cytochalasin B, [4-$^{3}$H]-; Daunomycin, [$^{3}$H(G)]-; Daunorubicin; Desipramine; Desmethylimipramine hydrochloride, [2,4,6,8-$^{3}$H]-; Diazald Diazepam; 2-([2,6-Dichloro-4-amino]phenylimino)-imidazoline; Diethyl-8-phenylxanthine, 1,3-[phenyl-4-$^{3}$H]-; Dihydroalprenolol hydrochloride, levo-[propyl-1,2,3-$^{3}$H]-; Dihydroalprenolol hydrochloride, levo-[ring, propyl-$^{3}$H(N)]-; Dihydroalprenolol, [nonanamide-6,7,9-$^{3}$H(N)]-; [Dihydro-a-ergocryptine,9,10-$^{3}$H(N)]-; Dihydromorphine, [N-methyl-$^{3}$H]-; Dihydropicrotoxinin, α-[8,10-$^{3}$H]-; Dithydrostrychnine, [21,22-$^{3}$H]-; Dilantin; [2,6-Dimethoxyphenoxyethyl]aminomethyl-1,4benzodi-oxane, 2-[phenoxy-3-$^{3}$H(N)] (WB4101); Dimethylbenz[a]anthracene, 1,12-[dimethyl-$^{14}$C]-; (1,3-Dimethylbutyl)-5-ethylbarbituric acid, (−)-5-[butyl-2,3,4-$^{3}$H]-; Dimethylhydrazine dihydrochloride, N,N-[methyl-$^{14}$C]-; Dinitrosopiperazine, N,N-[$^{14}$C(U)]-; Dioxolane, L ( )-cis,[2-methyl-$^{3}$H]-; Diphenylthydantoin, 5,5-[4-$^{14}$C]-; Diphenythydantoin, 5,5[phenyl-4-$^{3}$H(N)]-; (−)-DMBB and (+)-DMBB; Domperidone, [benzene ring-$^{3}$H]-; Doxepin, (methyl-$^{3}$H]-; Enkephalinamide (2-D-alanine-5L-methionine), [tyrosyl-3,5-$^{3}$H]-; Enkephalin (2-D-alanine-5D-leucine), [tyrosyl-3,5$^{3}$H(N)]-; Enkephalin (5-L-leucine), [tyrosyl-3,5-$^{3}$H(N)]-; Enkephalin (5-L-leucine), [$^{125}$I]-; Enkephalin (5-L-methionine), [tyrosyl-3,5-$^{3}$H(N)]-; Enkephalin (5-L-methionine), [$^{125}$I]-; Epidermal growth factor, [$^{125}$I]-; Ethyl β-carboline-3-carboxylate, [ethyl-2-$^{3}$H]-; Ethylketazocine; Ethylketocyclazocine, [9-$^{3}$H]-; Ethyl- 5-(1-methylbutyl)barbituric acid, 5-[ring-2-$^{14}$C]-; Ethyl-N-nitrosourea, N-[ethyl-1-$^{14}$C]-; Ethyl-5-phenylbarbituric acid, 5-[ring-2-$^{14}$C]-; Ethyl-5-phenylbarbituric acid 5-[$^{3}$H(G)]-; Fibronectin, [$^{125}$I]-; Flunitrazepam, [methyl-$^{3}$H]-; Fluorouracil, 5-[6-$^{14}$C]-; Flurazepam, [ethylene$^{3}$H]-; Gelatin, [$^{125}$I]-; Gibberellin A$_{1}$, [3,4-$^{3}$H(N)]-; Glucagon, [$^{125}$I]-(monoiodinated); Gonadotrophin releasing hormone; Haloperidol, [$^{3}$H(G)]-; Halothane, [1-$^{14}$C]-; Heparin, sodium salt [$^{3}$H(G)]-; Hexabromobiphenyl, 2,4,5,2',4',5'-[$^{14}$C(U)]-; Hexachlorobenzene, [$^{14}$C(U)]-; Hexachlorobiphenyl, 2,4,5, 2',4',5'-[$^{14}$C(U)]-; Hippuryl-L-histidyl-L-leucine, [glycine-1-$^{14}$C]-; Histamine dihydrochloride, [ring,methylenes-$^{3}$H(N)]-; Human chorionic gonadotropin, [$^{125}$I]-; Human growth hormone, [$^{125}$I]-; Hydroxyacetanilide, -p-[$^{3}$H(G)]-; Hydroxybenzyl-isoproterenol, p-[7-$^{3}$H]-; Hydroxybenzylpindolol, [$^{125}$I]-; Imipramine hydrochloride, [2,4,6,8-$^{3}$H]-; Imipramine hydrochloride, [N-methyl-$^{3}$H]-; Insulin (porcine)[$^{125}$I]-(monoiodinated); Iodoantipyrine, 4-[N-methyl-$^{14}$C]-; Iodoantipyrine, 4-[$^{125}$I]-; Iodoantipyrine, 4-[$^{131}$I]-; Iodohydroxybenzylpindolol, [$^{125}$I]-; Isoguvacine hydrochloride, [$^{3}$H]-; Isosorbide dinitrate, [$^{14}$C]-; Lidocaine hydrochloride, [carbonyl-$^{14}$C]-; Lindane; LSD; Luteinizing hormone releasing hormone, [pyroglutamyl-3,-4H]-; Luteinizing hormone releasing hormone, [$^{125}$I]-; Lysergic acid diethylamide, [N-methyl-$^{3}$H]-; Melanotropin release inhibiting hormone, [L-proline-2,3,4,5-$^{3}$H]-; Melatonin; Mepyramine; Methadone hydrobromide, levo-[1-$^{3}$H]-; Methotrexate, [L-glutamyl-3,4-$^{3}$H]-; Methscopolamine; Methyl β-carboline-3-carboxylate, [methyl-$^{3}$H]-; Methylcholanthrene, 3-[6-$^{14}$C]-; Methyl-D-aspartic acid, N-[methyl-$^{3}$H]-; Methyl mercury chloride, [$^{203}$Hg]-; Methyl-N'-nitro-N-nitrosoguanidine, N-[methyl-$^{14}$C]-; Methyl-N'-nitroso-p-toluenesulfonamide, N-[methyl-$^{14}$C]-; Methyl-N-nitrosourea, N-[methyl-$^{14}$C]-; Methyl-N-nitrosourea, N-[methyl-$^{3}$H]-; Methyl-2-phenylethyladenosine, L-N$^{6}$-1-[adenine-2,8H,ethyl-2-$^{3}$H]-; Methyl-N-vanillyl-nonanamide; 2-Methyl-4-trimethylammoniummethyl-1, 3-dioxolane iodide; Mianserin hydrochloride, [N-methyl-$^{3}$H]-; MIF; Morphine, [N-methyl-$^{3}$H]-; MTX; Muscimol, [methylene-$^{3}$H(N)]-; Naloxone, [N-allyl-2,3-$^{3}$H]-; Neurotensin, [3,11-tyrosyl-3, 5-$^{3}$H(N)]-; Nicotine, [pyrrolidine-2-$^{14}$C]-; Nicotine, DL-[pyrrolidinyl-$^{3}$H(N)]-; Nipecotic acid, [ring-$^{3}$H]-; Nitrendipie, [5-methyl-$^{3}$H]-; Nitrosodie-thylamine, N-[ethyl-1-$^{14}$C]-; Nitrosodimethylamine, N-[methyl-$^{14}$C]-; Nitrosoethylmethylamine, N-[ethyl-1-$^{14}$C]-; Nitroso methylurea; Nitrosonornicotine, N'[pyrrolidine-2-$^{14}$C]-; Nitrosopiperidine, N-[2,6-$^{14}$C]-; Nitrosopyrrolidine, N-[2,5-$^{14}$C]-; N-Methyl scopolamine; Oxotremorine-M acetate, [methyl-$^{3}$H]-; Pantothenic acid, sodium salt, D-[1-$^{14}$C]-; Paracetamol; Parathion, [phenyl-$^{14}$C]-; P[Pargyline hydrochloride, [phenyl-3, benyl-$^{3}$H]-; Pentobarbital; Phencyclidine, [piperidyl-34-$^{3}$H(N)]-; Phenobarbital; Phenoxybenzamine hydrochloride, [phenoxy-$^{3}$H(N)]-; Phenylisopropyl-adenosine; Phenytoin, Phorbol-12, 13dibutyrate, [20-$^{3}$H(N)]-; Phorbol-12-myristate-13-acetate, [20-$^{3}$H(N)]-; Piperiine-4 sulfonic acid, [ring-$^{3}$H]-; Polychlorinated biphenyls (isomeric mixture), [$^{14}$C(U)]-; Polychlorinated biphenyls (isomeric mixture), [$^{14}$C(U)]-; Prazosin, [turoyl-5-$^{3}$H]-; Prolactin (human), [$^{115}$I]-; Prolactin (rat), [$^{125}$I]-; Prolyl-leucyl-glycinamide; Propranolol, L-[4-$^{3}$H]-; Propyl β-carboline-3-carboxylate, [propyl-2,3-$^{3}$H]-; Propylnorapomorphine, L-(−)[N-propyl-$^{3}$H (N)]-; Pyrilamine, [pyrindinyl-5-$^{3}$H]-; Quinuclidinyl benzilate, L-[benzillic-4,4-$^{3}$H(N)]-; Rauwolscine, [methyl-$^{3}$H]-; Reserpine, [benzoyl-$^{3}$H(G)]-; Reverse T3; RO5-4864, [N-methyl-$^{3}$H]-; Salicyclic acid, [7-$^{14}$C]-; Scopolamine methyl chloride, [N-methyl-$^{3}$H]-; SXF-10,047, [N-allyl-2, 3-$^{3}$H]-; Somatostatin, 1-tyrosine, [$^{125}$I]-monoiodinated; Spiperone, [benzene ring-$^{3}$H]-; Spiroperidol; substance P (8-L-tyrosine), [$^{125}$I]-; Succinimidyl proplonate, N-[propionate-2,3-$^{3}$H]-; Sulfanilic acid, [$^{35}$S]-; Taurine, [$^{35}$S]-; Tetracycline, [7-$^{3}$H(N)]-(free base); Tetrahydroisoxazolo(5,4-c)pyridin-3-ol,4,5,6,7-[5,7-$^{3}$]-(THIP); Theophylline, [8-$^{14}$C]-; Thyroid stimualting hormone (human), [$^{125}$I]-; Thyrotropin releasing hormone, [L-proline-2,3,4,5-$^{3}$H(N)]-; Thyrotropin releasing hormone (3-methyl-histidine-), [L-histidyl-4-$^{3}$H(N)]-; L-prolyl-3,4-$^{3}$H(N)]-; Thyrotropin releasing hormone, [$^{125}$I]-(monoiodinated); Thyroxine, L-[$^{125}$I]-; Tiotidine, [methyl-$^{3}$H]-(ICI 125,211); Trifluoro-2-bromochloroethane; Trilodothyronine, L-3,5,3'-[$^{125}$I]-; Trilodothyronine, L-3,3', 5'-[$^{125}$I]-(Reverse T3); Tubocurarine chloride, dextro[13,-

$^3$H(N)]-; Valium (Trademark of Hoffmann-LaRoche); Vasopressin, 8-arginine, [$^{125}$I]-;. Vitamine A$_1$(all trans), [1-$^3$H(N)]-; WB-4101; Xylocaine; Yohimbine, [methyl-$^3$H]-.

The stabilizing compounds in accord with the present invention are particularly effective, with for instance, nucleoside and deoxynucleoside 5'-(α-thio)triphosphates such as deoxyadenosine 5'-(α-thio)triphosphate, [$^{35}$S]-, (dATPαS); and uridine 5'-(α-thio)triphosphate, [$^{35}$S]-, (UTPαS); nucleoside and deoxynucleoside 5'-triphosphates such as adenosine 5'-triphosphate, [α-$^{32}$P]-, (ATP); uridine 5'-triphosphate, [α-$^{32}$P]-; deoxyadenosine 5'-triphosphate, [α-$^{32}$P]-, (dATP) deoxycytidine 5'-triphosphate, [α-$^{32}$P]-; amino acids such as L-methionine, [$^{35}$S]- and L-leucine, [$^3$H]-; and peptides such as Substance P, [$^3$H]-.

Radiolabeled compounds are typically commercially distributed in closed vials containing a solution of the particular radiolabeled compound. The stabilizing compound is simply added to a solution of the radiolabeled compound which is typically shipped in a sealed vial from which the stabilized compound is removed by withdrawing with a syringe or pipette.

The invention will be further illustrated by the following examples, which are intended to be purely exemplary of the use of the invention.

EXAMPLES

In the examples below, solutions were prepared with various different radiolabeled compounds and stabilizer compounds. Radiochemical purity was determined initially and after storage by HPLC separation of the impurities followed by post-column radioactivity quantitization. The analytical system for each labeled compound was that described in the technical data sheet supplied with that compound. The purity values listed are the averages of determinations on duplicate samples.

All radiolabeled compounds were commercially available products manufactured by DuPont NEN Research Products (Boston, Mass.).

| GLOSSARY: | | |
|---|---|---|
| Blue dye | = | Patent Blue VF from Aldrich Chemical Co. (Milwaukee, WI) (Acid Blue 1, C.I. 42045) |
| DTT | = | dithiothreitol |
| EDTA | = | ethylenediaminetetraacetic acid |
| RT | = | rooin temperature(approximately 22° C.) |
| Tricine | = | N-tris(hydroxymethyl)methylglycine |
| Tris | = | tris(hydroxymethyl)aminomethane |
| — | = | not tested |

Example 1

[$^{35}$S]dATPαS at 21 mCi/ml and 1400 Ci/mmol was stored at room temperature in 5 mM Tricine—NaOH buffer, pH 7.6, containing 0.5 mM DTT and the stabilizer compounds listed below at the concentrations given.

The initial purity was 99%.

| Stabilizer Compound | Stabilizer conc. [mM] | Purity at Number of Days Stored | | |
|---|---|---|---|---|
| | | 10 | 18 | 34 |
| None | | 31 | 10 | — |
| Trithiocyanuric acid, Tris salt | 25 | 94 | 90 | 88 |
| 2-Mercaptopyridine | 50 | 87 | 76 | 73 |
| 4-Mercaptopyridine | 50 | 84 | 82 | 78 |
| 2-Mercaptonicotinic acid, Tris salt | 50 | 92 | 89 | 84 |
| 3-Aminothiophenol, Tris salt | 50 | 93 | 90 | 83 |
| Dimethyldithiocarbamic acid, Tris salt | 50 | 95 | 93 | 91 |
| Thiosemicarbazide | 50 | 92 | 87 | 85 |
| Dithiobiurea | 50 | 93 | 89 | 86 |

Example 2

[$^{35}$S]dATPαS at 18 mCi/ml and 1400 Ci/mmol was stored at the temperatures indicated below in 10 mM Tricine—NaOH buffer, pH 7.6, containing 1 mM DTT and the stabilizer compounds listed below at the concentrations given.

The initial purity was 95%.

Stabilizer 2A=5 mM trithiocyanuric acid, Tris salt

Stabilizer 2B=25 mM thiosemicarbazide

Stabilizer 2C=25 mM 4-sulfonylphenyl isothiocyanate, sodium salt

Stabilizer 2D=25 mM Rhodanine acetic acid, Tris salt

| °C. | Stab. | Purity at Number of Days Stored | | | | | | | |
|---|---|---|---|---|---|---|---|---|---|
| | | 7 | 14 | 28 | 39 | 49 | 61 | 83 | 125 |
| −30 | none | 94 | 94 | 93 | 94 | 88 | 89 | 84 | 77 |
| | 2A | 97 | 97 | 98 | 97 | 96 | 96 | 97 | — |
| | 2B | — | 97 | 98 | 98 | 97 | 96 | 96 | 96 |
| | 2C | — | 97 | 97 | 98 | 97 | 97 | 96 | — |
| | 2D | — | 98 | 95 | 97 | 96 | 97 | 96 | — |
| 4 | none | 76 | 51 | 11 | — | — | — | — | — |
| | 2A | 92 | 89 | 84 | 85 | 73 | 72 | 57 | — |
| | 2B | 93 | 88 | 86 | 86 | 83 | 82 | 83 | 86 |
| | 2C | 90 | 88 | 77 | 78 | 72 | 69 | 63 | — |
| | 2D | 97 | 94 | 87 | 91 | 86 | 86 | 82 | — |
| RT | none | 78 | 62 | 36 | — | — | — | — | — |
| | 2A | 94 | 88 | 60 | 56 | 32 | — | — | — |
| | 2B | 93 | 89 | 88 | 86 | 81 | 81 | 78 | 69 |
| | 2C | 92 | 88 | 84 | 84 | 78 | 73 | 32 | — |
| | 2D | 91 | 89 | 85 | 87 | 83 | 79 | 71 | — |

Example 3

[$^{35}$S]dATPαS at 18 mCi/ml and 1428 Ci/mmol was stored at room temperature in 10 mM Tricine—NaOH buffer, pH 7.6, containing 1 mM DTT, 0.3 mg/ml blue dye, and the thiosemicarbazide (TSC) analog stabilizers listed below at the concentrations given.

The initial purity was 93%.

| Stabilizer | Stabilizer conc. [mM] | Purity at Number of Days Stored 7 | 22 |
|---|---|---|---|
| None | | 77 | 50 |
| TSC | 25 | 93 | 91 |
| 4-MorpholinoethylTSC | 25 | 92 | 92 |
| 4-MethylTSC | 25 | 94 | 92 |
| 4,4-DimethylTSC | 25 | 92 | 86 |
| Acetone thiosemicarbazone | 10 | 92 | 87 |

Example 4

This example illustrates the ability of thiosemicarbazide to stabilize [$^{35}$S]dATPαS during shipment without refrigeration, and survive exposure to temperatures that might be encountered during summer in a delivery van or warehouse.

[$^{35}$S]dATPαS at 18 mCi/ml and 1428 Ci/mmol was stored at the temperatures indicated in 20 mM Tricine—10 mM Tris buffer, 5 mM Na$^+$, pH 7.6, containing 1 mM DTT, 10 μM EDTA, 0.3 mg/ml blue dye, and 25 mM thiosemicarbazide. The initial purities are shown at time=0. The control without thiosemicarbazide was at 40° C.

| °C. | Purity at Number of Days Stored | | | | | | | | | | |
|---|---|---|---|---|---|---|---|---|---|---|---|
| | 0 | 1 | 2 | 3 | 4 | 5 | 6 | 7 | 11 | 14 | 18 |
| 40* | 99 | — | — | 55 | 48 | 41 | — | 37 | 23 | — | — |
| 41 | 98 | 96 | 95 | 93 | 93 | — | — | 91 | 88 | 87 | 84 |
| 53 | 98 | 91 | 88 | 86 | 84 | — | — | 77 | 70 | 64 | 58 |
| 65 | 98 | 77 | 70 | 60 | — | — | 39 | — | — | — | — |

*Control

Example 5

[$^{35}$S]UTPαS at 49 mCi/ml and 876 Ci/mmol was stored at the temperatures indicated in 10 mM Tricine—NaOH buffer, pH 7.6, containing 1 mM DTT and the stabilizer compounds listed below at the concentrations given.

The initial purity was 95%.

Stabilizer 5A=5 mM trithiocyanuric acid, Tris salt
Stabilizer 5B=25 mM thiosemicarbazide
Stabilizer 5C=25 mM 4-sulfonylphenyl isothiocyanate, sodium salt

| °C. | Stab. | Purity at No. of Days Stored | | | | |
|---|---|---|---|---|---|---|
| | | 7 | 14 | 21 | 28 | 42 |
| −30 | none | 89 | 86 | 81 | 75 | 72 |
| | 5A | 92 | 92 | 92 | 91 | 89 |
| | 5B | 93 | 95 | 92 | 94 | 91 |
| | 5C | 94 | 93 | 87 | 89 | 86 |
| 4 | none | 21 | — | — | — | — |
| | 5A | 84 | 76 | 57 | 39 | — |
| | 5B | 86 | 82 | 76 | 72 | 70 |
| | 5C | 80 | 77 | 66 | 71 | — |
| RT | none | 16 | — | — | — | — |
| | 5A | 83 | 74 | 52 | 32 | — |
| | 5B | 82 | 80 | 74 | 72 | 59 |
| | 5C | 85 | 87 | 72 | — | — |

Example 6

Nucleoside[α-$^{32}$P]triphosphates at 10 mCi/ml and 3000 Ci/mmol were stored at 4° C. in 50 mM Tricine—Tris buffer, pH 7.6, containing the stabilizer compounds listed below at the concentrations given.

Stabilizer 6A=25 mM thiosemicarbazide
Stabilizer 6B=25 mM 4-sulfonylphenyl isothiocyanate, sodium salt

| Nucleotide | Stabilizer | Purity at Number of Days Stored | | | |
|---|---|---|---|---|---|
| | | 0 | 7 | 14 | 21 |
| ATP | none | 99 | 86 | 69 | 61 |
| | 6A | 99 | 91 | 82 | 76 |
| | 6B | 99 | 89 | 78 | 74 |
| UTP | none | 93 | 79 | 70 | 70 |
| | 6A | 93 | 89 | 84 | 83 |
| dATP | none | 95 | 84 | 78 | 66 |
| | 6A | 95 | 92 | 87 | 85 |
| | 6B | 95 | 90 | 85 | 80 |
| dCTP | none | 86 | 74 | 74 | 58 |
| | 6A | 86 | 81 | 83 | 78 |
| | 6B | 86 | 82 | 73 | 72 |

Example 7

L-[$^{35}$S]Methionine at 14 mCi/ml and 1000 Ci/mmol was stored for three weeks at the temperature indicated in 50 mM Tricine—NaOH buffer, pH 7.4, containing the stabilizer compounds listed below at a concentration of 25 mM.

The initial purity was 90%.

| Stabilizer | Purity After 3 Weeks | | |
|---|---|---|---|
| | −20° C. | 4° C. | RT |
| none | 70 | 1 | 1 |
| 2-Mercaptonicotinic acid, Tris salt | 88 | 86 | 81 |
| 2,5-Dithiobiurea | 84 | 84 | 67 |
| 2-Mercaptoimidazole | 85 | 86 | 82 |
| 2-Mercapto-1-methylimidazole | 87 | 87 | 86 |
| 4-Amino-2-mercaptopyrimidine | 73 | 85 | 84 |
| 2-Mercaptopyrimidine | 87 | 85 | 82 |
| 4-Mercaptopyridine | 89 | 80 | 80 |
| 2-Mercaptopyridine | 89 | 84 | 80 |

Example 8

L-[$^3$H]Leucine at 5.0 mCi/ml and 152 Ci/mmol was stored at 4° C. in water with the stabilizer compounds listed below at the concentrations given.

The initial purity was 100%.

Stabilizer 8A=10 mM 2-mercaptonicotinic acid, Tris salt
Stabilizer 8B=12.5 mM 2-mercapto-1-methylimidazole

| Stabilizer | Purity at No. of Days Stored | | |
|---|---|---|---|
| | 14 | 28 | 42 |
| none | 99.3 | 97.9 | 95.4 |
| 8A | 100 | 100 | 99.4 |
| 8B | 99.9 | 99.8 | 99.1 |

Example 9

[$^3$H]Substance P at 0.1 mCi/ml and 200 Ci/mmol was stored at −20° C. in a mixture of 0.1N acetic acid and ethanol (8:2 v/v) containing 1% 2-mercaptoethanol and the stabilizer compound listed below at the concentration given.

The initial purity was 98%.
Stabilizer 9A=25 mM 2-mercapto-1-methylimidazole

| Stabilizer | Purity at Number of Days Stored | | |
|---|---|---|---|
|  | 21 | 35 | 56 |
| none | 90 | 86 | 81 |
| 9A | 96 | 95 | 94 |

What is claimed is:

1. A method of stabilizing a solution of an organic compound labeled with a β-emitting radionuclide against radiolytic degradation during storage and shipment which comprises adding to said solution a separate, stabilizing effective amount of a non-radiolabeled stabilizing compound which does not bind to said labeled organic compound, said stabilizing compound being selected from the group consisting of (i) heteroaryls having at least one nitrogen atom, said heteroaryl being substituted with at least one sulfur-containing moiety selected from the group consisting of thiol and thiocarbonyl provided that the nitrogen atoms are not adjacent to one another; (ii) aryls being substituted with at least one nitrogen-containing moiety selected from the group consisting of amino and isothiocyanate and with at least one sulfur-containing moiety selected from the group consisting of sulfonamide, sulfonate, and thiol; and (iii) alkylamines having at least one to four carbon atoms, said alkylamine being substituted with at least one sulfur-containing moiety selected from the group consisting of thioacid and thiocarbonyl provided that when the sulfur-containing moiety is a thioacid then the aminoalkyl contains only one nitrogen atom.

2. A method according to claim 1 wherein the heteroaryl stabilizing compound of (i) is selected from the group consisting of trithiocyanuric acid, 2-mercaptonicotinic acid, 2-mercaptoimidazole, 2-mercapto-1-methylimidazole, 4-amino-2-mercaptopyrimidine, 2-mercaptopyrimidine, 4-mercaptopyridine, and 2-mercaptopyridine.

3. A method according to claim 1 wherein the aryl stabilizing compound of (ii) is selected from the group consisting of aminobenzene sulfonamide, 3-aminothiophenol and 4-sulfonyl phenyl isothiocyanate.

4. A method according to claim 1 wherein the alkylamine stabilizing compound of (iii) is selected from the group consisting of dimethyldithiocarbamic acid, thiosemicarbazide, 4-morpholinoethyl-thiosemicarazide, 4-methyl-thiosemicarbazide, 4,4-dimethylthiosemicarbazide, acetone thiosemicarbazone and 2,5-dithiobiurea.

5. A method according to claim 1 wherein the radionuclide is selected from the group consisting of $^3$H, $^{14}$C, $^{32}$P, $^{33}$P, $^{35}$S, and $^{125}$I.

6. A method according to claim 1 wherein the radiolabeled organic compound is selected from the group consisting of an amino acid, peptide, nucleotide, polypeptide, oligonucleotide, polynucleotide, carbohydrate, protein, nucleoside, steroid, lipid, fatty acid, or catecholamine.

7. A method according to claim 1 wherein the stabilizing effective amount of stabilizer is at a concentration of 0.1 mM to 200 mM.

8. A method of stabilizing a solution of an organic compound labelled with a β-emitting radionuclide against radiolytic degradation during storage and shipment which comprises adding to said solution a stabilizing effective amount of rhodanine-3-acetic acid.

* * * * *